(12) United States Patent
Datta et al.

(10) Patent No.: US 6,218,326 B1
(45) Date of Patent: Apr. 17, 2001

(54) SUPPORTED MOLTEN-METAL CATALYSTS

(75) Inventors: Ravindra Datta; Ajeet Singh; Istvan Halasz; Manuela Serban, all of Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/124,419

(22) Filed: Jul. 29, 1998

(51) Int. Cl.$^7$ .............. B01J 35/12; B01J 35/10; B01J 23/42
(52) U.S. Cl. .............. 502/3; 502/250; 502/262; 502/303; 502/304; 502/313; 502/328; 502/325; 502/329; 502/332; 502/334; 502/339; 502/527.24
(58) Field of Search .............. 502/3, 325, 339, 502/527.24, 250, 262, 313, 303, 304, 328, 329, 332, 334

(56) References Cited

U.S. PATENT DOCUMENTS

| | | | |
|---|---|---|---|
| 3,855,307 | * 12/1974 | Rony et al. | 502/161 |
| 4,187,200 | * 2/1980 | Jenkin | 252/472 |
| 4,576,926 | * 3/1986 | Wang et al. | 502/339 |
| 4,713,360 | * 12/1987 | Newkirk et al. | 501/87 |
| 4,898,845 | * 2/1990 | Datta et al. | 502/3 |
| 5,385,689 | * 1/1995 | Tom et al. | 502/402 |
| 5,387,565 | * 2/1995 | Taylor, Jr. | 502/63 |
| 5,432,142 | * 7/1995 | Smith | 502/344 |
| 5,486,628 | * 1/1996 | Kemp | 549/536 |
| 5,531,971 | * 7/1996 | Tom et al. | 423/210 |
| 5,589,602 | * 12/1996 | Smith et al. | 585/671 |
| 5,849,966 | * 12/1998 | Smith et al. | 585/363 |
| 5,929,275 | * 7/1999 | Wada et al. | 562/545 |
| 5,981,820 | * 11/1999 | Smith et al. | 585/671 |

FOREIGN PATENT DOCUMENTS

1185453 * 3/1970 (GB) .

* cited by examiner

Primary Examiner—Elizabeth D. Wood
(74) Attorney, Agent, or Firm—Zarley, McKee, Thomte, Voorhees & Sease (57) ABSTRACT

An entirely new class of catalysts called supported molten-metal catalysts, SMMC, which can replace some of the existing precious metal catalysts used in the production of fuels, commodity chemicals, and fine chemicals, as well as in combating pollution. SMMC are based on supporting ultra-thin films or micro-droplets of the relatively low-melting (<600° C.), inexpensive, and abundant metals and semimetals from groups 1, 12, 13, 14, 15 and 16, of the periodic table, or their alloys and intermetallic compounds, on porous refractory supports, much like supported microcrystallites of the traditional solid metal catalysts. It thus provides orders of magnitude higher surface area than is obtainable in conventional reactors containing molten metals in pool form and also avoids corrosion. These have so far been the chief stumbling blocks in the application of molten metal catalysts.

7 Claims, 5 Drawing Sheets

SUPPORTED MOLTEN-METAL CATALYSTS

GRANT REFERENCE

This application is based in part on funding received from DOE under grant number DE-FG02-96ER12184, and the government may have certain rights in this invention.

BACKGROUND OF THE INVENTION

Heterogeneous catalysts are of central importance in the fossil fuel refining, and synthesis of alternative fuels, chemicals, and fine chemicals, as well as in environmental applications, e.g., automotive exhaust treatment, and resource and energy conservation (Campbell, I. M., *Catalysis at Surfaces,* Chapman and Hall, 1988; National Research Council, *Catalysis Looks to the Future,* National Academy Press, Washington, D.C., 1992; Ribeiro, F. H., and Somorjai, G. A., "Heterogeneous Catalysis by Metals", in King, R. B., ed. *Encyclopedia of Inorganic Chemistry,* Vol. 3, p. 1359, John Wiley, New York, 1994). It has been estimated that the value of goods processed through catalysis is roughly 1 trillion dollars, or about 20% of the gross national product. However, there still are a number of challenges that remain to be addressed in the design of more efficient and cheaper catalysts. The functions of a catalyst include facilitating reactions under milder conditions, increasing selectivity of the desired reactions, and providing a large interfacial area to reduce the precious metal usage and reactor volume. The conventional heterogeneous catalysts are based on microcrystallites of transition metals supported on porous supports and frequently involve precious metals such as Pt, Pd, Rh, Ir, Ru, etc. These transition metal catalysts presumably act by providing degenerate electronic states involving unfilled d-electron orbitals and can, thus, bind with a variety of species by readily donating or accepting electrons (Somorjai, G. A., "The Building of Catalysts. A Molecular Surface Science Approach", in Hegedus, et al., eds., *Catalyst Design. Progress and Perspectives,* John Wiley, New York, 1987; Somorjai, G. A., *Introduction to Surface Chemistry and Catalysis,* John Wiley, New York, 1994; Masel, R. I., *Principles of Adsorption and Reaction on Solid Surfaces,* John Wiley, New York, 1996). Further, the common reactant gases such as $H_2$, $O_2$, $N_2$ and CO are atomized by these metals for supply to the reacting species, the bond strength of H, C, N, and O to the metal providing the thermodynamic driving force for the atomization. The best catalysts are those that form bonds of intermediate strength with adsorbates. If the binding is too strong, further reaction is discouraged. On the other hand, if the binding is too weak, reaction rates are too low.

The catalysts also provide the surface geometry and configuration conducive to reaction. Thus, different reactions require site ensembles of different size and are classified as "structure sensitive" or "structure insensitive". Thus, besides altering the electronic characteristics, alloying of a metal with another reduces the multiple atom ensembles, thus altering rates of structure sensitive reactions, and hence selectivity. Further, the supported microcrystallites of solid metals possess different crystal faces as well as steps and kinks on the surface, thus providing a variety of catalytic sites of diverse electronic properties and coordination. As a result, heterogeneous catalysts often have a limited selectivity to the desired product and resistance to poisoning and deactivation, resulting in a substantial waste of chemicals and energy.

On the other hand, homogeneous catalysts (liquid phase) are promising because of their higher catalyst activity and product selectivity, milder operating conditions and better control of the nature of catalytic species. The commercial importance of such catalysts has been established by the success of the Wacker process for acetaldehyde and the oxo process, as well as the so-called Monsanto process for acetic acid. It has been found that homogeneous catalysts consisting of transition metal complexes catalyze a variety of reactions with greater selectivity and activity than the conventional solid catalysts. However, the applications of homogeneously catalyzed reactions in industry are still quite limited due to some engineering problems associated with them. Separation of the homogeneous catalysts from the reaction mixture is often difficult, and high catalyst recovery must be achieved. Lack of effective catalyst utilization in conventional gas-sparged reactor, corrosion problems and catalyst contamination in the product are among the other disadvantages of homogeneous catalysis. Many of the disadvantages of heterogeneous catalysts can be eliminated, while retaining many of the advantageous features of homogeneous catalysts through the process of "heterogenizing" the catalysts by dispersing them in the pores of a solid support or by binding them to a polymer substrate.

In recent years, there have been numerous attempts to "heterogenize" some homogeneous catalyst so that the resulting catalysts would have the advantages of both homogeneous and heterogeneous catalysts. Some of these techniques include Polymer Bound Catalysts, Immobilized Enzyme System, Supported Liquid Phase Catalysis (SLPC), Supported Aqueous-Phase Catalysis (SAPC), Supported Aqueous-Phase Enzymatic Catalysis (SAPEC), and Supported Molten Salt Catalysis (SMSC). None of these, however, have so far met with great success. Supported molten metal catalyst technique is based on the concept of physically heterogenizing homogeneous catalyst.

Some of the drawbacks of traditional solid metal catalysts, such as sintering, limited selectivity, and coking may be addressed by the use of molten metal catalysts, which are functionally like heterogeneous solid catalysts in that catalysis proceeds on the surface of the molten metal through chemisorption and surface reaction but, unlike heterogeneous solid catalysts, have uniform and fluid surface sites. Molten metal catalysis also differs from traditional homogeneous liquid-phase catalysis, in which gaseous reactants dissolve in the liquid phase and undergo bulk liquid-phase reaction.

The catalytic properties of liquid metals and alloys have been studied by many investigators since the turn of this century. Ipatiew, W., *Ber.,* 34, 1047,1901 found that metallic zinc catalyzed the decomposition of alcohols above its melting point. His work thus showed that molten metals possess catalytic activity. Hartman, R. J., and O. W. Brown, Catalytic Activity of Cadmium, *J.Phys.Chem.,* 34,2651, 1930 found that molten lead, thallium and bismuth gave high yields of aniline from nitrobenzene. They also reported that cadmium could make an excellent catalyst for the reduction of nitrobenzene to aniline. They observed that the cadmium metal prepared from different cadmium salts had different catalytic activities. Hydrogenation of nitrobenzene showed a maximum at the melting point of Cd metal. They explained these results on the basis of Taylor's concept of active centers, which would presumably disappear upon melting of the metal. Steacie, E. W. R., and E. M. Elkin, *Proc.R.Soc.London,* A142, 457,1933 investigated the catalytic activity of pure zinc above and below its melting point for the thermal decomposition of methyl alcohol. The result showed no sharp decrease or break of the catalytic activity at the melting point of zinc. Adadurow, I. E. and P. D.

Didenko, *J.Am.Chem.Soc.*, 57,2718,1935 conducted the catalytic oxidation of ammonia by fusion of metallic tin and silver. For the experiments with tin as catalyst, no abrupt change in the catalytic activity was observed at the melting point of tin (231.8° C.). However, it was theorized that the catalyzing effect was obtained not by metallic tin, but by tin oxide which was formed by the reaction of tin and air. Adadurow and Didenko (1935) also attempted the decomposition of methyl alcohol by zinc chips at 360° C. to 400° C. and found that the zinc chips were covered by zinc oxide layer on their surface. Schwab, G. M. and H. H. Martin, *Z.Elektrochem.*,43,610,1937 examined the role of active centers at the melting point of the catalyst metals. They argued against Steacie's result and showed that pure zinc liquid was inactive, and that only the zinc contaminated by oxygen was active for their reaction. In 1950, Weller and his co-workers studied liquid tin as a coal liquefaction catalyst. They made comparative catalyst tests for the hydrogenation of coal. Zinc, when tested in the presence of ammonium chloride, showed appreciable catalytic activity. It was found possible to replace at least 90% of the tin in a tin ammonium chloride catalyst by zinc without appreciable loss of catalytic effectiveness. Other catalysts, such as ferrous sulfate, pyrite, and red mud, were found to be less active in comparison with tin plus ammonium chloride or zinc plus ammonium chloride in promoting coal liquefaction. Friedman, S., Kaufman, M. L. and I. Wender, Alkali Metals as Hydrogenation Catalysts for Aromatic Molecules, *J.Org.Chem.*,36,694,1971 examined the hydrogenation of polynuclear aromatic compounds over alkali metals at high temperatures and pressures. The alkali metals, such as Na, K and binary alloys Na—K, Na—Rb and Na—Cs exhibited high catalytic activity. Catalytic activity increased from lithium to rubidium. Schwab, G. M., *Ber. Bunsenges Phys. Chem.*,80,746,1976 studied the catalysis by liquid alloys. He measured the rate of decomposition of formic acid over Hg-based binary alloys and Tl-based binary alloys. He interpreted the experimental results on the basis of the electron theory of alloys in the solid state.

Since the early work described above, significant advances in the field of molten metal catalysis have been made. In fact, Ogino and coworkers have done much of the more recent work in this area (Ogino, Y., *Catalysis and Surface Properties of Liquid Metals and Alloys,* Marcel Dekker, Inc., New York, 1987). Catalytic activities of various metals and semi-metals such as Na, K, Zn, Cd, Hg, Al, Ga, In, Tl, Sn, Pb, Sb, Bi, Te and Se with the melting point in the range of −39° C. to 660° C. have been studied in the molten state by Ogino, 1987. Some of the binary alloys such as Na—K, Na—Rb, and Na—Cs have also been studied. Ogino and co-workers (Ogino, A., Catalysis by Molten Metal and Molten Alloys, *Catal Rev-Sci. Eng.*,23,505,1981 and Ogino,Y., *Catalysis and Surface Properties of Liquid Metals and Alloys,* Marcel Dekker, Inc., New York, 1987) found many molten metals to be highly selective and stable. The various types of reactions investigated by Ogino and co-workers (Ogino, 1987) include dehydrogenation of alcohols, amines, and hydrocarbons, hydrogenation of hydrocarbons, hydrogen transfer reactions, and coal liquefaction. None of these reactions or of the Ogino literature describes supported molten metal catalysts.

A characteristic feature of the liquid metal catalyst is the absence of frozen defects or disordered elements on the surface, which are important in determining the catalytic activity and selectivity of solid metal catalysts. The problem of deactivation of conventional metal catalysts due to sintering and catalyst fouling can also be reduced by the use of liquid metal catalysts. These liquid metal catalysts are also much less expensive as compared to the conventional transition noble metal catalysts and are easy to prepare.

In spite of the above-mentioned prospects and advantages, liquid metals have not yet been used as industrial catalysts due to some significant engineering problems associated with them. The molten metal catalyst has so far typically been used in bulk or pool form. When used in this form, there are severe limitations on the rate of reaction due to the very small interfacial area obtained. This greatly reduces the effectiveness of catalyst utilization and requires large reactors for a given conversion. Further, handling and corrosion with molten metals are very serious problems. These stumbling blocks, however, can be effectively overcome in the practice of the present invention.

It is accordingly a primary object of the present invention to provide an entirely new class of catalysts called supported molten metal catalysts (SMMC) which may replace some existing precious metal catalysts to provide more efficient and economical catalytic reaction systems.

Another object of the present invention is to provide a supported molten metal catalyst, which is a combination of a molten metal and a porous support that is inert to the molten metal such that much more surface is exposed to allow catalytic reactions to occur on the larger exposed surface, resulting in levels of three to four orders of magnitude increased rates of reaction.

It is another object of the present invention to provide low-melting metal catalysts with porous supports in which the molten metal is an alloy comprising of two or more metals.

An even further object of the present invention is to provide low melting point metal catalysts on porous support surfaces in which the metal has dispersed crystallites of other metals or their compounds contained within it.

The method and manner of accomplishing each of the above objectives, as well as others, will become apparent from the detailed description of the invention which follows hereinafter.

BRIEF DESCRIPTION OF THE DRAWINGS

In the Figures, the abbreviation SMMC stands for supported molten metal catalyst.

SUMMARY OF THE INVENTION

Supported molten metal catalysts are made and demonstrated as being useful in a variety of catalytically-controlled commercial chemical reactions. The result of the support is that the molten metal catalyst does not pool, and much more surface is exposed to allow the catalytic reaction to occur on the larger exposed surface. The result can be 3–4 orders of magnitude increased rate for catalytic reactions. The supports are conventional porous support materials and can, for example, be silica, alumina, or other commercial supports. The metal is placed on the internal surface of the support as micro-droplets or is spread in a thin film. The reactants enter the pores and react on the molten metal catalyst surface. Because of the nature of the supported molten metal matrix, the amount of surface for reaction is much larger per given amount of catalysts than unsupported molten metal, providing more efficient catalysis. In addition, the support can chemically enhance the catalytic reaction.

DETAILED DESCRIPTION OF THE INVENTION

Figure 1:
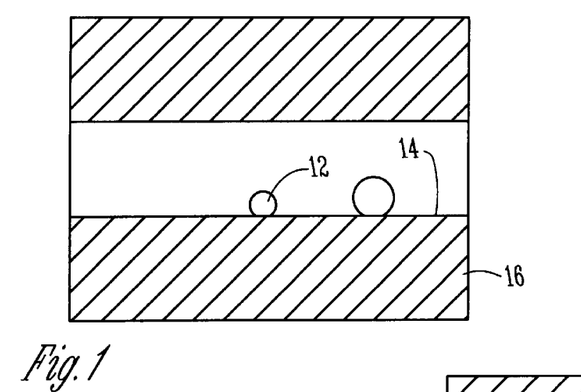
FIG. 1 is a schematic showing a porous support with molten metal droplets on its internal surface.
Figure 2:
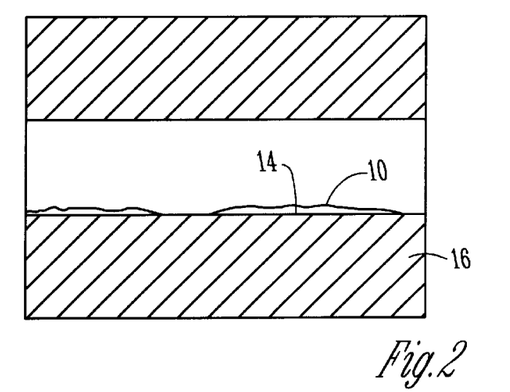
FIG. 2 is a schematic showing a porous support with a thin molten metal film on its internal surface.
Figure 3:
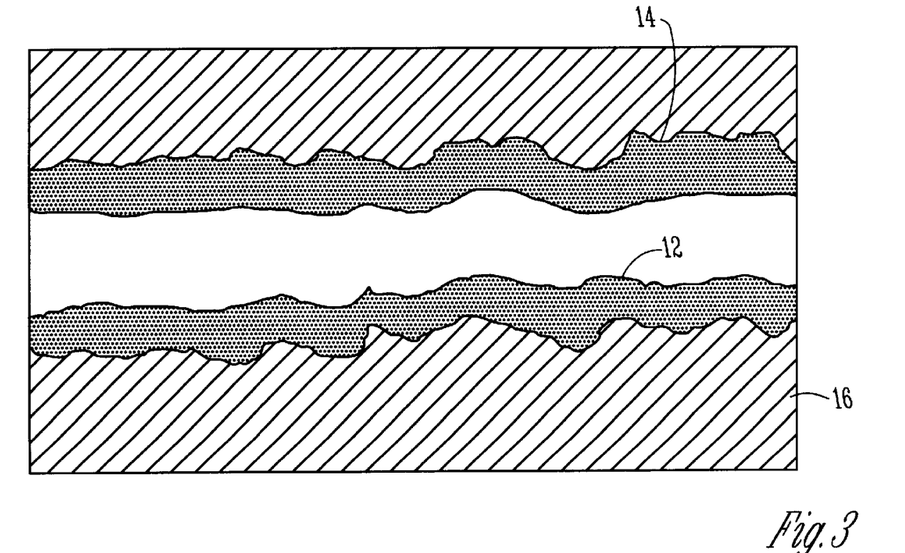
FIG. 3 is a schematic of a supported molten metal catalyst with a higher metal loading.

In the technique of supported molten metal catalysis of the present invention, microdroplets 12 or a thin film (about 5–10 nm) of the molten metal catalyst is coated on the large internal surface area 14 of porous supports 16 (see FIGS. 1, 2 and 3). Various techniques known in the art for catalyst preparation processes such as impregnation followed by reduction, melt deposition, vapor deposition, etc., can be used to coat the molten metal on the internal surface of porous support 14. The molten metals and semi-metals suitable for coating are the more abundant, less expensive, relatively low melting elements from groups 1, 12, 13, 14, 15 and 16 of the periodic table. These molten metals are held inside the porous support by Van der Waals and other forces. The term molten metal as used here includes molten pure metals, metal alloys and metals with dispersed particles of solid metals or their compounds. The reactants diffuse through the residual pore space and react on the surface of the molten metal catalyst. Crystallites of solid metal and/or metal compound catalysts may also be dispersed in molten metal catalyst for rate or selectivity enhancement through synergism or for bifunctional catalysis. In addition, the support may possess a catalytic function. The crystallites of metals suitable for dispersion may be conventional catalysts such as platinum, palladium, rhodium, nickel, silver, etc. Metals or alloys that melt below the reaction temperature and have low volatility at the reaction temperature are suitable for the present invention. A large variety of molten metals, alloys, and intermetallic compounds are available with melting points ranging from below room temperature to well above 1000° C. Some of the possible molten metals and alloys that may be used in supported molten metal catalyst system are given in Tables 1 and 2. However, there are numerous other possibilities, as given for example by Moffatt, W. G., *The Handbook of Binary Phase Diagrams*, Genium Publishing, Schenectady, N.Y., 1984.

TABLE 1

Some of the Possible Molten Metal Catalysts Suitable for Use in the Invention

| Metals | Melting Point (° C.) | Boiling Point (° C.) |
|---|---|---|
| Hg | −38.9 | 357 |
| Ga | 29.8 | 1700 |
| K | 63.4 | 757 |
| Na | 97.5 | 800 |
| In | 155 | 1450 |
| Li | 186 | 1336 |
| Se | 217 | 649 |

TABLE 1-continued

Some of the Possible Molten Metal Catalysts Suitable for Use in the Invention

| Metals | Melting Point (° C.) | Boiling Point (° C.) |
|---|---|---|
| Sn | 232 | 2260 |
| Bi | 271 | 1450 |
| Tl | 303 | 1650 |
| Cd | 321 | 767 |
| Pb | 327 | 1620 |
| Zn | 419 | 907 |
| Te | 449.5 | 989.8 |
| Sb | 631 | 1380 |
| Mg | 651 | 1110 |
| Al | 660 | 2057 |

TABLE 2

Some of the Possible Low-Melting Metal Alloy Catalysts Suitable for SMMC System

| Alloy | Composition (Wt. %) | Melting Point (° C.) |
|---|---|---|
| Cs—Rb | 87:13 | −40 |
| Cs—Na | 95:5 | −30 |
| K—Na | 78:22 | −11 |
| Rb—Na | 92:8 | −8 |
| Ga—In—Sn | 62.5:21.5:16.0 | 10.7 |
| Ga—Sn—Zn | 82:12:6 | 17 |
| Na—K | 40:60 | 27 |
| Rb—K | 68:32 | 33 |
| In—Bi—Sn | 51.0:32.5:16.5 | 60.5 |
| Na—Rb | 60:40 | 67 |
| In—Sn | 49:51 | 120 |
| In—Cd | 75:25 | 120 |
| Bi—Sn—Pb | 46.1:34.2:19.7 | 123 |
| Bi—Pb | 55.5:44.5 | 124 |
| Bi—Sn—Zn | 56:40.4 | 130 |
| Bi—Sn | 58:42 | 140 |
| Bi—Cd | 60:40 | 140 |
| In—Zn | 97.8:2.2 | 143.5 |
| Li—Pd | 32:68 | 145 |
| Sn—Pb | 38:62 | 183 |
| Tl—Bi | 52:48 | 185 |
| Sn—Pb | 70:30 | 192 |
| Sn—Zn | 92:8 | 199 |
| Sn—Cu | 99.25:0.75 | 227 |
| Na—In | 20:80 | 267 |
| Na—Pb | 30:70 | 386 |

The molten metal film may be continuous or fragmented, depending upon wetting characteristics and the liquid catalyst loading q, which is defined as the fraction of void volume occupied by the molten catalyst. For homogeneous catalysts where the reaction occurs within the bulk volume, it is found that the optimal value of liquid loading in supported liquid phase catalysts (SLPC) is in the range, q=0.3–0.5 (Datta, R., and R. G. Rinker, Supported Liquid-Phase Catalysis:I. A theoretical Model for Transport and Reaction, *J.Catal.*, 95,181,1985a). There is not enough catalyst available at lower q, while at higher q, diffusion through the pore space becomes limiting. This is in contrast to the case in supported molten metal catalysis of the present invention, since the reaction is confined to the surface rather than throughout the volume. Thus, the optimal liquid loading corresponds to the lowest q required for a monolayer on the pore surface. At higher loadings the surface area, and consequently the reaction rate, declines. Further, pore blockage can occur at the higher loadings. On the other hand, loadings corresponding to less than complete coverage may be desirable, particularly for bifunctional catalysts in which the support surface also possesses a catalytic function.

The supported molten metal catalysis technique offers several advantages. First, high catalytic activity per unit mass of the molten metal catalyst results due to almost complete dispersion, owing to the thinness (5–10 nm) of the catalyst film or micro-droplets, as compared with usage in the bulk form; second, high rates of reaction per unit volume of reactor result, once again due to the high efficiency of catalyst utilization; third, there is almost a complete absence of corrosion problems since the molten metal is confined within the pores of the refractory support and does not come in direct contact with the reactor walls (in fact, the pellets retain a dry appearance); fourth, the technique offers atomically uniform surface for catalysis unlike conventional heterogeneous solid metal catalysts that contain substantial surface heterogeneity (which could possibly mean improvement in selectivity); fifth, no sophisticated techniques are necessary for preparing the catalysts; sixth, the deactivation due to sintering, common in solid metal catalysis, is avoided; seventh, the deactivation due to carbonaceous deposition is less pronounced due to the mobile nature of the catalyst film; eighth, the molten metal catalysts are typically more abundant and less expensive as compared to the traditional transition metal catalysts; and, ninth, since catalyst sites are mobile, it is conceivable that reaction rates and selectivities of reactions involving multiple sites could be enhanced.

The technique of supported molten metal catalysts can be classified into three subgroups depending upon the relationship between the molten metal and the support. In the first sub-class, the molten metal, alloy, or intermetallic compound is coated inside the pores of a support (FIG. 2). The thin layer or micro-droplets of molten metal acts as the active catalyst. The porous support 16 is inert, and solely acts to disperse the molten metal. Alternatively, its interaction with molten metal may serve to enhance the catalytic activity of the latter. In the second sub-class of supported molten metal catalysts, the support is not inert, and in addition to its role in the dispersion of the catalyst, possesses a catalytic function on its own, e.g., acid or basic function. Thus, such a supported molten metal catalyst would be bifunctional and of use in reactions such as reforming where both the metal function and support function are essential in catalysis. Clearly, the liquid loading in this case must be low so that the support surface is also accessible. In the third sub-class of supported molten metal catalysts, the microcrystallites of a solid metal or its compound is dispersed in a molten metal film supported on a porous support. In this system, microcrystallites of solid metal or metal salt act as the active catalyst. The molten metal film acts either as a co-catalyst or simply as a medium for the dispersion of micro-crystallites of metal or metal compounds.

A variety of commercially available porous supports of different surface areas, pore size distribution, and surface properties can be used for the preparation of supported molten metal catalysts, depending upon the type of reaction and the molten metal catalyst. It is, of course, desirable for the molten metal to not react with the support. The wetting of support by the liquid metal is also an important criterion for supported molten metal catalyst preparation. For coating a thin film of liquid metal on porous support surface, the molten metal must wet the surface. Otherwise, the molten metal would form drops or stay in a pool form inside the pores of the support. Table 3 shows exemplary supports.

TABLE 3

Some of the Possible High Melting Supports Suitable for SMMC System

| Type | Supports | Melting Point (° C.) |
|---|---|---|
| Basic | MgO | 3073 |
|  | CaO | 2853 |
|  | $Ca_2SiO_4$ | 2407 |
|  | BaO | 2196 |
|  | $Ca_3SiO_5$ | 2173 |
| Amphoteric | $ThO_2$ | 2323 |
|  | $ZrO_2$ | 2988 |
|  | $CeO_2$ | 2873 |
|  | $Cr_2O_3$ | 2708 |
|  | $La_2O_3$ | 2588 |
|  | $Al_2O_3$ | 2318 |
|  | $TiO_2$ | 2133 |
| Neutral | $MgAl_2O_4$ | 2408 |
|  | $ZnCr_2O_4$ | 2173 |
|  | $ZnAl_2O_4$ | 2100 |
|  | $CaSiO_3$ | 1813 |
|  | $MgCr_2O_4$ | 2300 |
|  | Honeycomb |  |
| Acidic | $\gamma$-$Al_2O_3$ (High Surface Area) | 2318 |
|  | $SiO_2$(High Surface Area) | 1973 |
|  | $SiO_2$—$Al_2O_3$ (High Surface Area) | 1818 |
|  | Zeolites, Pillared Clays |  |
| Other | Carbon, Nitrides, Carbonates, Sulfates |  |

Actually, good dispersion may be obtained even for a non-wetting molten metal (with contact angle >90°) at low catalyst loadings, when it would form micro-droplets on the surface, much like supported solid microcrystallites. The liquid metal could also possibly interact with the support either by chemical or physical interaction. For supported molten metal catalysts, of primary interest is the liquid metal-support system having no chemical interaction, although it is conceivable that in some systems this may be desirable. Further, as mentioned above, bifunctional catalysis, in which the support is also catalytic, is also feasible. For such cases, however, the molten metal catalysts loading must be low enough so that an adequate fraction of the support surface is also accessible. The supported molten metal catalyst technique can be applied to a large number of reactions. For organic materials these include, but are not limited to, selective dehydrogenation, hydrogenation, cyclodehydrogenation, isomerization, hydroisomerization, hydrocracking, reforming, partial oxidation, halogenation, dehalogenation, oxychlorination, hydrodesulfunization, hydrodenitrogenation, oxidative dehydrogenation, and water-gas shift reaction, etc.

The methods for SMM catalyst preparation are fairly simple. A number of different methods such as solution impregnation followed by reduction, melt imbibition, and vapor deposition can be used for the catalyst preparation. The suitability of various methods would very much depend upon the type of molten metal and the support used. Supported molten metal catalysts can be prepared for instance by liquid-phase impregnation. The objective is to fill the pores with a solution of metal salt of sufficient concentration to give the desired loading. The support can be used either in particle or pelletized form. The catalyst supports may be first heated or evacuated by placing in vacuum for about 6–8 hours in order to remove the moisture/air from the voids. This is not an essential step, but speeds diffusion of the solute into the pore. Known amounts of a salt of the metal compound such as oxide, sulfide or chloride, are dissolved in a compatible liquid solvent. The solubility of the salt must be sufficient to give convenient volumes at prescribed temperatures. Water is the preferred solvent, but if necessary, other aqueous or organic solvents could be used. The amount of solvent is determined by the quantity of deposited salt desired, size of laboratory vessels, and requirements of other steps in the preparation. This may be calculated from measured pore volume, but is sometimes more reliably determined by trial and error.

In a next step, evacuated/dehydrated catalyst supports are immersed in the prepared solution. When these catalyst supports are immersed in the solution, it is imbibed into the pores of the support due to capillary suction, and at the same time impregnant diffusion and adsorption starts. This time dependent flow of the impregnating solution reaches the center of the pellets relatively quickly, and after that only diffusion and adsorption continue for a much longer period. The pellets are usually left in the solution for about 24 hours. After that, the supports are removed from the solution and wiped off lightly to remove excess solution. The liquid solvent is dried off by placing the pellets in a vacuum oven at about 100° C. for about 12 hours. Drying is necessary to crystallize the salt on the pore surface. The rate of drying is an important step in the preparation of conventional heterogeneous metal catalyst. The supported metal salt inside the pore is then reduced to active metal catalyst by passing hydrogen, or other appropriate gaseous or liquid reducing reagent, over the catalyst support at an elevated/room temperature. In this manner, particles of metal catalyst are deposited on the pore walls of the porous supports. The amount of metal catalyst deposited on pore walls is obtained by weight gain of the pellets. The metal loaded pellets are then heated above the melting point of the metal in an inert atmosphere. In this manner, micro-droplets or a thin layer of molten metal catalyst is deposited on the pore walls of the support.

A similar method may be applied for dispersing the crystallites of transition metal in the molten metal film. The evacuated support pellets are immersed in a solution carrying the compounds of molten metal and the transition metal together or sequentially. Next, the pellets are dried and metal compounds reduced to active metals.

Melt imbibition is a simple albeit crude method of supported molten metal catalyst preparation. In this method, appropriate amounts of catalyst support and metal catalyst in powder form are mixed together and are loaded into a suitable tubular reactor. The reactor is then purged with helium gas overnight to displace air. This mixture is next heated in this inert atmosphere above the melting point of the metal catalyst. The molten metal comes directly in contact with porous support which allows molten metal uptake by capillary action and dispersion by surface tension. The amount of loaded catalyst can be calculated by the weight gain. In Vapor Deposition method, the catalyst support and metal catalyst are heated in a closed inert atmosphere at a temperature high enough to produce sufficient vapor pressure of the metal catalyst. These metal vapors then diffuse into the pores of the support, and on cooling, get deposited on the pore walls of the support. However, the metal catalyst should produce sufficient vapor pressure at reasonable temperatures; otherwise this method may not be practical. The resulting catalyst loading is usually low and dependent upon vapor pressure of the metal catalyst and diffusion time or contact time between vapor and support. In some cases it may be desirable to have multiple vapor depositions to achieve the desired catalyst loading. It is evident that the reaction temperature for these catalysts, while above their melting point, should not be high enough to cause substantial catalyst volatility and concomitant loss.

A number of different reactions have been investigated to establish the broad efficacy of the technique and to study the key advantages as well as limitations. Based on the examples cited below, the supported molten metal catalyst is shown to be a viable and attractive technique, leading to a new class of catalysts with many potential applications. The following examples are offered to illustrate, but not limit, the process of this invention.

EXAMPLE 1

Tetralin Dehydrogenation

This example demonstrates the dramatic enhancement in reaction rate as a result of increased dispersion and surface area in SMMC.

Tetralin dehydrogenation, chosen for this purpose, has been studied by Ogino and co-workers on liquid Te catalyst both in a bubbling type reactor (Takahashi, K., and Y. Ogino, Liquid Tellurium as a Catalyst for the Dehydrogenation of Several Polynuclear Hydrocarbons, *Chem. Lett.*, 423,1978), as well as in a duct reactor (Takahashi, K., and Y. Ogino, Studies on the Catalysis of Molten Metal 13. Kinetics of Dehydrogenation of Tetralin Over Molten Tellurium Catalyst, *Fuel*, 60,975,1981). The sequential reaction is illustrated below:

Since the surface area of the liquid Te catalyst in the duct reactor is known precisely, it is possible to calculate the turnover number, $N_T$, defined as the molecules of reactant converted per surface metal atom per second, from the experiments of Takahashi and Ogino. This was found to be in the range of $N_T$=10 to 118 in the temperature range of 508° C. to 570° C. It is of interest to compare this turnover number with that for the conventional transition metal catalysts. Although comparable numbers for this particular reaction were not found in the literature (Somorjai, G. A.,) *Introduction to Surface Chemistry and Catalysis*, John Wiley, New York, 1994) has summarized turnover numbers for the common hydrocarbon reactions on platinum catalysts. He gives an upper limit of $N_T$<100 for the dehydrogenation reactions. Thus, Te appears to be highly active in the dehydrogenation of tetralin.

Figure 4:
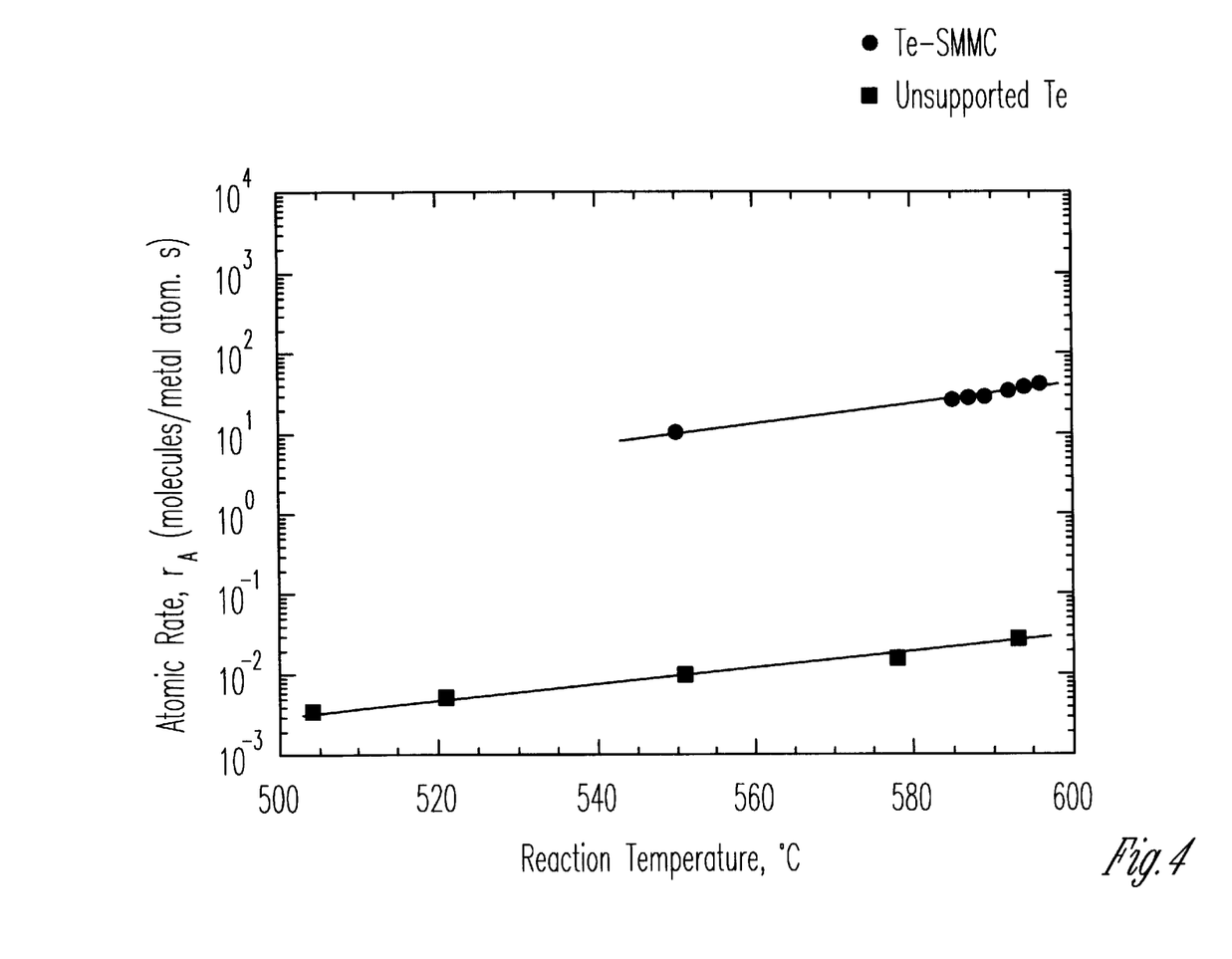
FIG. 4 is a comparison of unsupported liquid tellurium and 3% tellurium/aluminum oxide.

The dehydrogenation of tetralin on a Te-supported molten metal catalyst was studied in the temperature range of 530° C. to 595° C. by utilizing a 3% Te/$Al_2O_3$ catalyst. The results, in terms of an atomic rate, $r_A$, defined as molecules of reactant converted per bulk metal atom per second, are shown in FIG. 4 and are also compared with the data of Takahashi, K., and Y. Ogino, Liquid Tellurium as a Catalyst for the Dehydrogenation of Several Polynuclear Hydrocarbons, *Chem.Lett.*,423,1978.

In FIG. 4 it is seen that the atomic rate in Te-supported molten metal catalyst is 3 to 4 orders of magnitude higher than that in unsupported Te, clearly demonstrating the dramatic enhancement in rate as a result of the increased surface area of supported catalyst in supported molten metal catalyst, thus establishing the basic efficacy and soundness of rationale of the invention.

EXAMPLE 2

Ethanol Dehydrogenation

Figure 5:
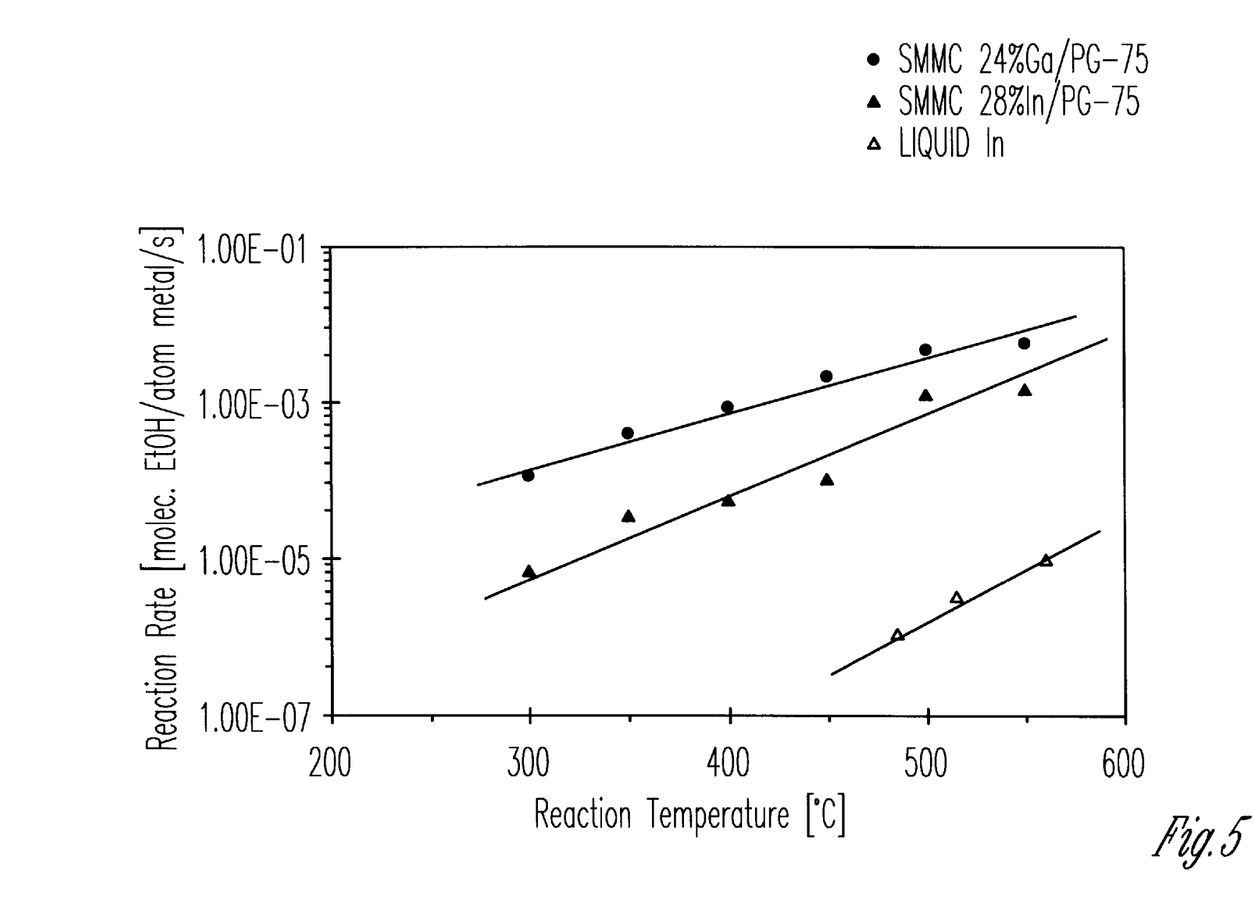
FIG. 5 is a comparison of unsupported liquid indium and indium and gallium supported molten metal catalysts used for ethanol dehydrogenation.

Ethanol dehydrogenation to produce acetaldehyde is an industrially significant reaction. In 1990, 340,000 t/6 of acetaldehyde was produced in the U.S. at a price of $1.02/kg. It is illustrated as follows:

Although the major current commercial route for acetaldehyde is the Wacker process involving ethylene oxidation, some acetaldehyde is also obtained from the oxidative dehydrogenation of ethanol using a silver catalyst at 480° C. If a process for producing $CH_3CHO$ from hydrous biomass-derived ethanol could be developed, it may prove to be commercially attractive. Thus, the vapor phase dehydrogenation of ethanol over a 28% In on porous glass (PG-75) and a 24% Ga/PG-75 was investigated. The results are shown in FIG. 5 and are also compared with those of (Saito, Y., Hiramatsu, N., Kawanami, N., and Ogino, Y., *Bull. Jap. Petrol. Inst.*, 14, 169, 1972) on liquid In. It is seen again that the rate can be enhanced by several orders of magnitude when the liquid metal catalyst is supported on a porous support, by virtue of the increase in surface area.

EXAMPLE 3

The above two examples demonstrate that the salt can be enhanced greatly for reactions previously studied on bulk molten metals.

Due to the dramatic increase in the metal surface area, however, it becomes possible to study reactions on supported molten metal catalyst which are too slow to be observed on the limited surface area of liquid metals in the conventional pool reactors. New bifunctional reactions are also feasible in which support plays a catalytic role. Some of these results are described here and in the next example.

Methylcyclohexane (MCH) dehydrogenation to form toluene is shown in the following reaction:

This is a very important reaction in catalytic reforming, with an estimated $10^8$ tons/y of methylcyclohexane being processed in reforming. The resulting production of toluene is accompanied by octane enhancement. MCH has also been suggested as a hydrogen carrier in automotive fuel cell applications. The conventional catalyst, $Pt/Al_2O_3$, for this is initially extremely active, but quickly deactivates due to coking. The reaction is ensemble size insensitive, but coking is ensemble size sensitive. Thus, alloying helps to reduce the deleterious effect of coking. For instance, the bimetallic Pt—Re catalyst on alumina support offers the best combination of initial activity and resistance to deactivation. MCH dehydrogenation on molten metals has not been observed so far due likely to the limited surface area available in pool reactors. Alternatively, this could be due to bifunctional catalysis involved in the reaction.

Figure 6:
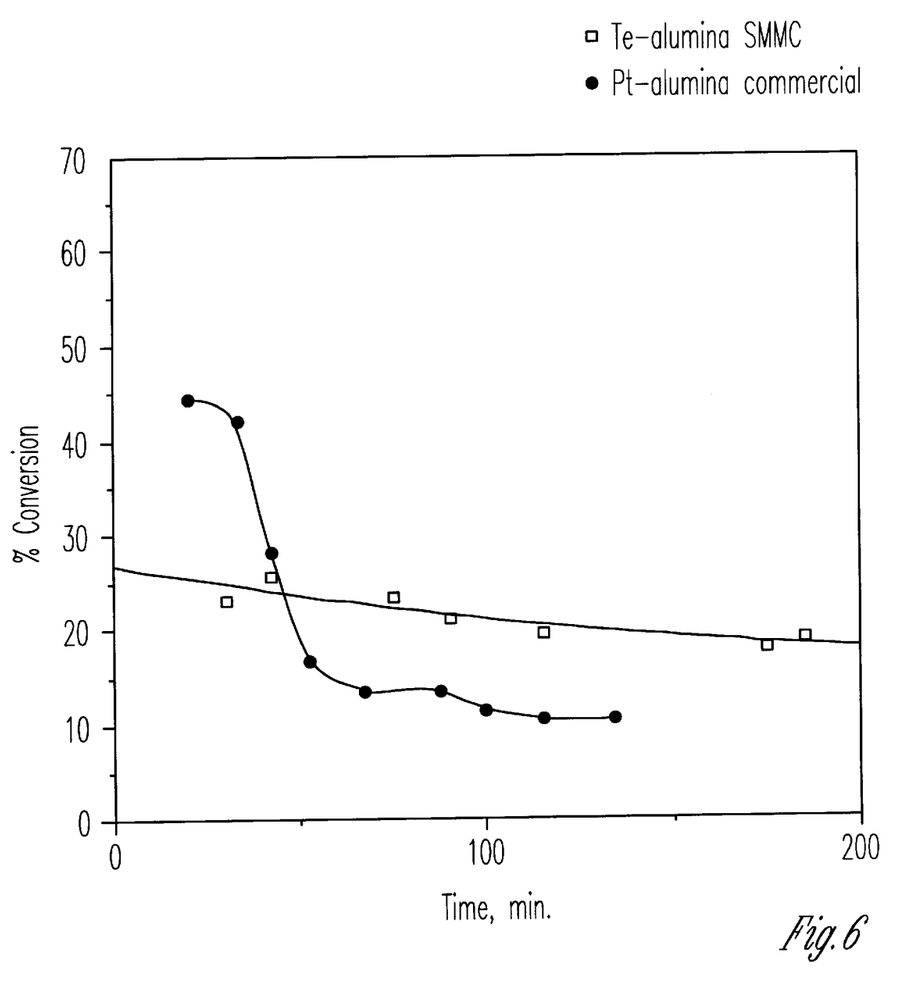
FIG. 6 is a comparison of tellurium-alumina and commercial platinum-alumina catalysts at 460° C., 10 atmospheres for methylcyclohexane dehydrogenation activity.

MCH dehydrogenation was studied on Te—$Al_2O_3$ catalyst prepared by mixing 2 g of —$Al_2O_3$ support with 1.8 gm of Te powder in an inert atmosphere and heating above the melting point for about 5 hours. In this manner, about 4% molten Te catalyst was dispersed on porous alumina pellet by imbibition as confirmed by the final weight gain. The resulting catalyst was tested for MCH dehydrogenation at 460° C. and 10 atm. About 2.4 gm of commercially-obtained 1% Pt—$Al_2O_3$ catalyst (Aldrich) was also tested under similar conditions to directly compare its performance to that of supported molten metal catalyst. The results are summarized in FIG. 6. In looking at FIG. 6, one can see that the reactivity of the two catalysts is of the same order, which is remarkable since $Pt/Al_2O_3$ is an extremely active catalyst for this reaction. For supported molten metal catalyst, a 25% decline in total conversion of MCH was observed as compared to 75% decline for 1% Pt—$Al_2O_3$ catalyst system over a 3 h period. Thus, although the initial activity of the commercial Pt catalyst was higher, the eventual activity of the supported molten metal Te catalyst was higher due to the lower susceptibility of catalyst to deactivation by coking. The final atomic rates calculated for the two catalysts are $r_A=3.2\times10^{-2}$ molecules/metal atom•s for $Pt/Al_2O_3$, while $r_A=2.5\times10^{-3}$ for $Te/Al_2O_3$. The MCH dehydrogenation is also catalyzed by a variety of other SMMCs listed in Table 1.

EXAMPLE 4

Minimizing $NO_x$ ($N_2O$, NO, and $NO_2$) emissions from various mobile and stationary combustion sources is an important environmental goal. Substantial $NO_x$ is emitted form diesel or gasoline engine powered automobiles, incinerators, boilers, combustion turbines, and numerous other sources. The environmental and health effects of $NO_x$ are well known. For example, $NO_x$ can aggravate chronic heart and respiratory diseases. It also contributes to the acid rainfall, ground level ozone, and depletion of the stratospheric ozone layer. Therefore, the 1990 Amendments to the Clean Air Act mandate significant reduction in the emission of, among other pollutants, nitrogen oxides by the year 2000. Since nitric oxide is the main pollutant, most deterious effects of $NO_x$ pollution can be minimized if NO is prevented from entering the atmosphere.

Catalytic reduction is a widely used method for lowering $NO_x$ emission. All current catalytic technologies aim to selectively reduce NO to $N_2$. Applicable reductants and catalysts vary depending on the oxygen content and origin of emission. In exhausts with low oxygen content and ample CO and $H_2$ supply, these latter molecules can be utilized for the reduction of NO, as typically done in three way catalysts (TWC) of gasoline engine powered automobiles.

If excess oxygen is present in the exhaust (net oxidizing condition), however, the reduction of NO by $H_2$ or CO becomes sluggish over all known catalysts because these reductants react more readily with $O_2$ than with NO. Exhausts of many stationary sources and vehicles powered with lean-burn gasoline and diesel engines are examples for $NO_x$ emission at net oxidizing conditions. A possible solution for the $NO_x$ removal from such oxygen-rich exhausts is the injection of a selective reductant which preferentially reacts with NO. For example, ammonia has been injected into the exhausts of various stationary $NO_x$ emission sources since the early 1960s. This process is called Selective Catalytic Reduction (SCR) and uses mostly platinum, vanadium pentoxide, or zeolite containing catalysts. However, the commercial SCR technology suffers from several difficulties, such as the "slip" of ammonia into the atmosphere and the poisoning of catalysts by coal ash particles or soot.

It was discovered in 1991 that hydrocarbons and oxygenated hydrocarbons, such as alcohols and oxo-compounds, can be used instead of nitrogen bases for the SCR of NO over Cu-ZSM5 catalyst. This new technique, denoted as HC-SCR, holds promise to overcome the current difficulties of $NO_x$ abatement from oxygen rich mobile and stationary exhaust. Therefore, there is enormous interest in developing a commercial HC-SCR catalyst. Despite a vast amount of research, however, no durable and effective commercial HC-SCR catalyst has yet been developed. One impediment to success is that there is no viable catalyst for these processes in the presence of $H_2O$ probably because water either saturates the active sites of catalysts or destroys the zeolite structure. Water, of course, is inevitably present in all combustion exhausts.

The best reported catalyst for the HC-SCR of NO by hydrocarbon in presence of substantial $H_2O$ is Fe-ZSM5. However, this catalyst reportedly works with i-butane which is relatively expensive and inconvenient to handle. Coking is also a problem. Thus, it is desirable to find a catalyst with non-zeolite structure which is active and selective for the HC-SCR of NO to $N_2$ by C1–C3 hydrocarbons or oxygenated hydrocarbons in the presence of $H_2O$.

Figure 7:
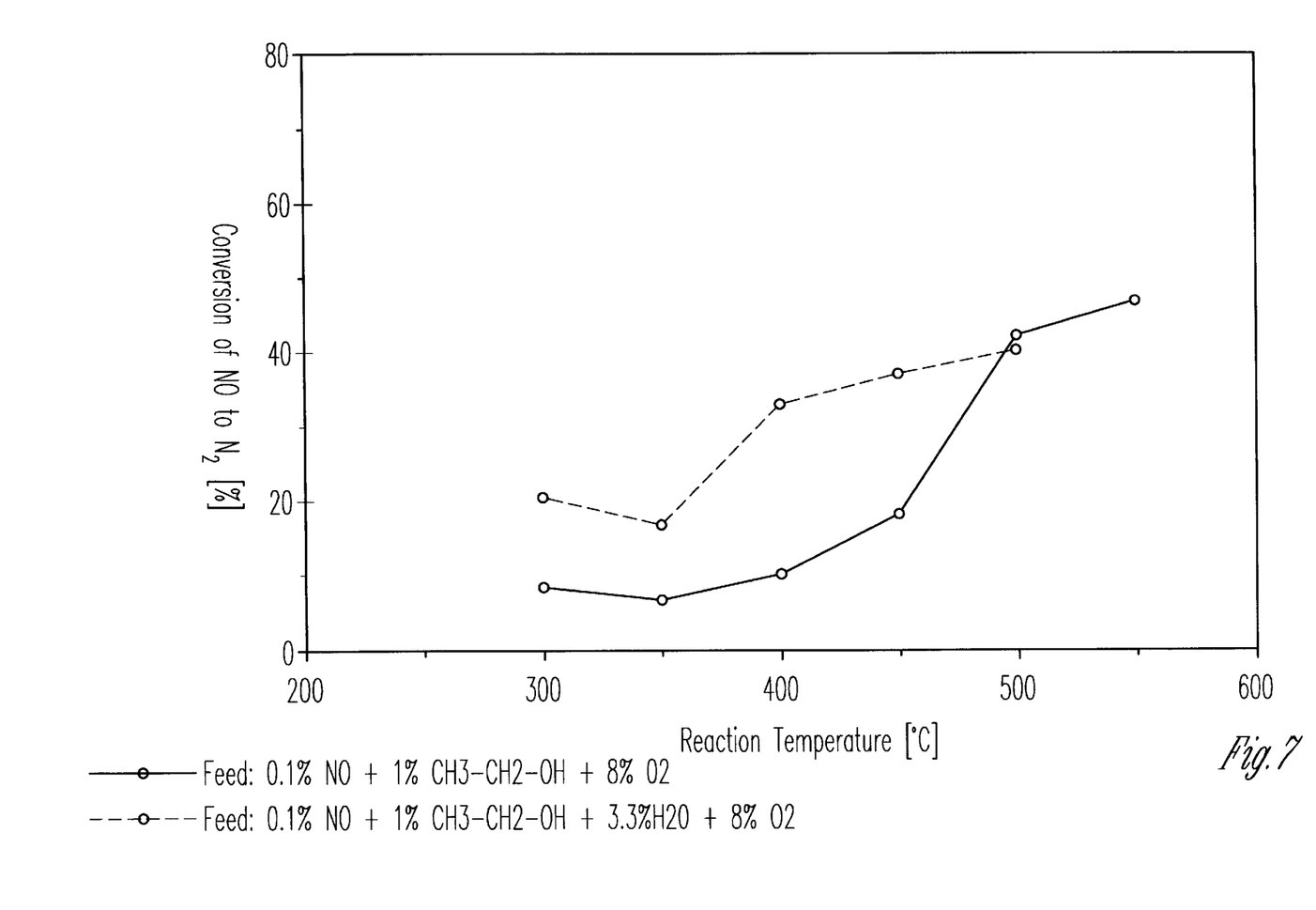
FIG. 7 is a comparison of indium-controlled pore glass catalyst reactivity for the selective catalytic reduction of nitric oxide by ethanol in oxygen rich environment in the presence and absence of water.

As curve a in FIG. 7 demonstrates, an SMMC catalyst composed of 28% indium supported on controlled pore glass (In-CPG-SMMC) was found to be quite active for the HC-SCR of NO to $N_2$ by ethyl alcohol at reaction conditions resembling those in catalytic converters of commercial exhausts. In contrast to most other catalysts, the catalytic activity of In-CPG-SMMC increased when the feed contained substantial amounts of water (FIG. 7, curve b). Despite the use of a $SiO_2$ (controlled pore glass) support, which is typically unsuitable carrier for highly active SCR catalysts, the In-CPG-SMMC proved to be more active for the ethanol based SCR of NO than other catalysts reported so far, including In-exchanged zeolites and supported indium oxide catalysts. These results demonstrate that supported molten metal catalysts may open up an entirely new avenue for developing commercially viable $NO_x$ abatement catalysts to treat oxygen rich exhausts in the presence of substantial water.

Also studied successfully for the present invention have been oxidative dehydrogenation of alcohols to produce the corresponding aldehydes and ketones on In and Ga supported molten metal catalyst. These reactions are of possible commercial interest and occur with good selectivity. Of course, there are innumerable other reactions of possible interest that may be catalyzed by SMMC.

From the above examples, the supported molten metal catalyst technique has been shown to be viable technique, leading to the development of a new class of catalysts. A rate enhancement of 3 to 4 orders of magnitude is possible as a result of the increase in the surface area by supporting, which also allows one to study reactions not previously observed on molten metals. As compared with conventional transition metal catalysts, supported molten metal catalysts are less active but more selective and stable. Consequently, it has numerous possible applications in selective oxidation and hydrogenation reactions, reactions involving N, S, and halogens, especially those reactions which are normally conducted at high temperature and in the presence of poisons. Further liquid phase reactions are also possible with SMMCs involving low melting catalysts.

It therefore can be seen that the invention accomplishes at least all of its stated objectives.

What is claimed is:

1. A supported molten metal catalyst in which a molten metal, which functions as a catalyst, is coated on the surface of a porous support said molten metal catalyst being selected so that it is molten under the reaction conditions of the process which it catalyzes wherein the molten metal is platinum.

2. The supported molten metal catalyst of claim 1 in which the molten metal is in the form of a thin film coating.

3. The supported molten metal catalyst of claim 1 in which the molten metal is in the form of microdroplets.

4. The supported molten metal catalyst of claim 1 in which the dispersed metal crystallites are selected from the transition metals vanadium, chromium, platinum, palladium, rhodium, nickel, silver, molybdenum, manganese, rhenium, iron, ruthenium, osmium, cobalt, and copper.

5. The supported molten metal catalyst of claim 1 in which the porous support is selected from the group consisting of MgO, CaO, $Ca_2SiO_4$, BaO, $Ca_3SiO_5$, $ThO_2$, $ZrO_2$, $CeO_2$, $Cr_2O_3$, $La_2O_3$, $Al_2O_3$, $TiO_2$, $MgAl_2O_4$, $ZnCr_2O_4$, $ZnAl_2O_4$, $CaSiO_3$, and $MgCr_2O_4$.

6. The supported molten metal catalyst of claim 1 in which the support is not inert and itself possesses a catalytic function.

7. A supported molten metal catalyst comprising molten metal coated on the surface of a porous support and microcrystallites of solid metal or metal compounds dispersed in the molten metal wherein the molten metal is molten under the reaction conditions of the process which the catalyst catalyzes and wherein the molten metal is platinum.

\* \* \* \* \*